(12) United States Patent
Kwok

(10) Patent No.: US 11,007,266 B2
(45) Date of Patent: May 18, 2021

(54) METHOD OF MITIGATING CARDIOVASCULAR HYPERTROPHY AND PERIVASCULAR FIBROSIS INDUCED BY ANGIOTENSIN II

(71) Applicant: UNIVERSITY OF MACAU, Macau (CN)

(72) Inventor: Hang Fai Kwok, Macau (CN)

(73) Assignee: University of Macau, Macau (CN)

( * ) Notice: Subject to any disclaimer, the term of this patent is extended or adjusted under 35 U.S.C. 154(b) by 170 days.

(21) Appl. No.: 16/032,482

(22) Filed: Jul. 11, 2018

(65) Prior Publication Data
US 2019/0015505 A1 Jan. 17, 2019

Related U.S. Application Data

(60) Provisional application No. 62/530,903, filed on Jul. 11, 2017.

(51) Int. Cl.
| | |
|---|---|
| *A61K 39/395* | (2006.01) |
| *A61K 45/06* | (2006.01) |
| *A61P 9/12* | (2006.01) |
| *C07K 16/40* | (2006.01) |
| *C07K 16/28* | (2006.01) |
| *A61K 39/00* | (2006.01) |

(52) U.S. Cl.
CPC .......... *A61K 39/3955* (2013.01); *A61K 45/06* (2013.01); *A61P 9/12* (2018.01); *C07K 16/2896* (2013.01); *C07K 16/40* (2013.01); *A61K 2039/505* (2013.01); *C07K 2317/76* (2013.01)

(58) Field of Classification Search
CPC ....... A61K 39/3955; A61K 45/06; A61P 9/12; C07K 16/2896; C07K 16/40
See application file for complete search history.

(56) References Cited

U.S. PATENT DOCUMENTS

2007/0134256 A1* 6/2007 Lai .................. C07K 16/1081
424/159.1

FOREIGN PATENT DOCUMENTS

| WO | WO-0127279 A1 * | 4/2001 | ............ C07K 16/28 |
| WO | WO-2012022734 A2 * | 2/2012 | ......... C07K 16/2821 |
| WO | WO-2012076066 A1 * | 6/2012 | ......... C07K 16/2803 |

OTHER PUBLICATIONS

Kawai et al. "Pharmacological Inhibition of ADAM17 by a Human-Cross Reactive Antibody and Selective Inhibitor JG26 Prevents Vascular Fibrosis . . . " American Heart Association archives, Pres. May 7, 2016 [Retrieved May 18, 2020 from https://aha.scientificposters.com/index.cfm?k=6hvtigq9p2], (Year: 2016).*

Alexander, R.W. "Hypertension and the Pathogenesis of Atherosclerosis". Originally published Feb. 1, 1995. Hypertension. 1995;25: 155-161 (Year: 1995).*

Tape, CJ. "Discovery and Development of Therapeutic Tace Antibodies", PhD dissertation, King's College, University of Cambridge, Jul. 2011 (Year: 2011).*

Akira Takaguri, et al.: ADAM17 mediates neointimal hyperplasia in vasculature: Hypertension. Apr. 2011; 57(4): 841-845. doi:10.1161/HYPERTENSIONAHA.110.166892.

Haruhiko Ohtsu, et al.: ADAM17 Mediates Epidermal Growth Factor Receptor Transactivation and Vascular Smooth Muscle Cell Hypertrophy Induced by Angiotensin II: Sep. 2006: e133-e137.

Katherine J. Elliott, et al.: ADAM17 silencing by adenovirus encoding miRNA-embedded siRNA revealed essential signal transduction by angiotensin II in vascular smooth muscle cells: J Mol Cell Cardiol. Sep. 2013: 62: 1-7: pp. 1-15: doi:10.1016/j.yjmcc.2013.05.005.

W. B. Melenhorst, et al.: ADAM17 upregulation in human renal disease: a role in modulating TGF-α availability?: Am J Physiol 297: F781-F790, 2009: First published Jun. 17, 2009; doi:10.1152/ajprenal.90610.2008.

Carl P. Blobel: ADAMS: Key Components in EGFR Signalling and Development: Jan. 2005: vol. 6: pp. 32-43.

Peiyong Zhai, et al.: An Angiotensin II Type 1 Receptor Mutant Lacking Epidermal Growth Factor Receptor Transactivation Does Not Induce Angiotensin II-Mediated Cardiac Hypertrophy: Circulation Research: Sep. 1, 2006: pp. 528-536.

Augusto C. Montezano, et al.: Angiotensin II and Vascular Injury: Curr Hypertens Rep (2014): pp. 1-11.

(Continued)

*Primary Examiner* — Joanne Hama
*Assistant Examiner* — Scott T. Humbarger
(74) *Attorney, Agent, or Firm* — Ladas & Parry LLP

(57) ABSTRACT

Angiotensin II (AngII) has been strongly implicated in hypertension and its complications. Evidence suggests the mechanisms by which angiotensin II (AngII) elevates blood pressure and enhances cardiovascular remodeling and damage may be distinct. In vascular smooth muscle cells, a metaloproteinase ADAM17 mediates epidermal growth factor receptor (EGER) transactivation, which may be responsible for cardiovascular remodeling but not hypertension induced by AngII. Treatment with a human cross-reactive ADAM17 inhibitory antibody (A9B8) also prevented cardiovascular, remodeling and ER stress but not hypertension in C57Bl/6 mice infused with AngII. In vitro data further supported these findings. In conclusion, vascular ADAM17 mediates AngII-induced cardiovascular remodeling via EGFR activation independent of blood pressure regulation. ADAM17 presents a unique therapeutic target for antibodies such as A9B8 for the prevention of hypertensive complications.

7 Claims, 6 Drawing Sheets
(3 of 6 Drawing Sheet(s) Filed in Color)

Specification includes a Sequence Listing.

(56) References Cited

OTHER PUBLICATIONS

Vaibhav B. Patel, et al.: Angiotensin II induced proteolytic cleavage of myocardial ACE2 is mediated by TACE/ADAM-17: A positive feedback mechanism in the RAS: Jan. 2014: vol. 66: pp. 167-176.
Takehiko Takayanagi, et al.: Caveolin-1 is critical for abdominal aortic aneurysm formation induced by angiotensin II and inhibition of lysyl oxidase: Clin Sci (Lond): Jun. 2014: 126(11): pp. 1-22. doi:10.1042/CS20130660.
Akira Takaguri, et al.: Caveolin-1 is critical for abdominal aortic aneurysm formation induced by angiotensin II and inhibition of lysyl oxidase: J Mol Cell Cardiol: Mar. 2011: 50(3): pp. 545-551: doi:10.1016/j.yjmcc.2010.12.009.
Hideo Kanaide, et al.: Cellular Mechanism of Vasoconstriction Induced by Angiotensin II it Remains to be Determined: Circulation Research: Nov. 28, 2003: pp. 1015-1017.
Haruhiko Ohtsu, et al.: Central Role of $G_3$, in the Hypertrophic Signal Transduction of Angiotensin II in Vascular Smooth Muscle Cells: Endocrinology 149(7): Jul. 2008 by the Endocrine Society: doi: 10.1210/en.2007-1694: pp. 3569-3575.
Hang Fai Kwok, et al.: Development of a 'mouse and human cross-reactive' affinity-matured exosite inhibitory human antibody specific to TACE (ADAM17) for cancer immunotherapy: Protein Engineering, Design & Selection vol. 27: No. 6: pp. 179-190, 2014: Published online Apr. 24, 2014 doi:10.1093/protein/gzu010.
Matthew R. Weir, et al.: Effects: of Renin-Angiotensin System Inhibition End-Organ Protection: Can We Do Better?: Clinical Therapeutics: vol. 29: No. 9: Sep. 2007: pp. 1803-1824.
Jianchun Chen, et al.: EGFR Signaling Promotes TGFβ-Dependent Renal Fibrosis, Journal of the American Society of Nephrology 23: pp. 215-224: 2012.
Kathryn M. Spitler, et al.: CHBPR: Endoplasmic Reticulum Stress Contributes to Aortic Stiffening via Pro-Apoptotic and Fibrotic Signaling Mechanisms: Department of Physiology, Geornia Regents University: Mar. 2014: pp. 1-15.
Takashi Obama, et al.: Epidermal growth factor receptor inhibitor protects against abdominal aortic aneurysm in a mouse model: Clinical Science (2015): 128: pp. 559-565.
Steven J. Forrester, et al.: EGFR transactivation: mechanisms, pathophysiology, and potential therapies in cardiovascular system: Author manuscript: 2016: pp. 1-27.
Hong Lian, et al.: Heparin-Binding EGF-Like Growth Factor Induces Heart Interstitial Fibrosis via an Akt/m/Tor/p70s6k Pathway: Sep. 12, 2012: vol. 7: Issue 9: pp. 1-10.
Allan D, Struthers, et al.: High B-Type Natriuretic Peptide Hypertensives at Target Blood Pressure Potential Role of β-Blockers to Reduce Their Elevated Risk: Hypertension: 2015: 66: pp. 927-932 DOI: 10.1161/HYPERTENSIONAHA.115. 06270.
John J. Lepore, et al.: High-Efficiency. Somatic Mutgenesis in Smooth Muscle Cells and Cardiac Myocytes in SM22α-Cre Transgenic Mice: 2005 Wiley-Liss, Inc.: Genesis 41: pp. 179-184 (2005).
Brent M. Egan, et al.: :Hypertension in the United States 1999-2012: Progress Toward Healthy People 2020 Goals: NIH-PA Author Manuscript: Nov. 4, 2014: 130(1): pp. 1-18.
Luuk te Riet, et al.: Hypertension Renin-Angiotensin-Aldosterone System Alterations: Circulatation Research: Mar. 13, 2015: pp. 960-975.
Edward E. Schmidt: et al., Illegitimate Cre-dependent chromosome rearrangements in transgenic mouse spermatids: Dec. 5, 2000 vol. 97: No. 25: pp. 13702-13707.
Barbara Schreier, et al.: Loss of Epidermal Growth Factor Receptor in Vascular Smooth Muscle Cells and Cardiomyocytes Causes Arterial Hypotension and Cardiac Hypertrophy: Feb. 2013: pp. 333-340.
Gisela Weskamp, et al.: Pathological neovascularization is reduced by inactivation of ADAM17 in endothelial cells, but not in pericytes NIH-PA Author Manuscript: Mar. 19, 2010; 106(5); pp. 1-22.
P. E. Morange, et al.: Polymorphisms of the tumor necrosis factor-alpha (TNF) and the TNF-alpha converting enzyme (TACE/ADAM17) genes in relation to cardiovascular mortality: the Athero Gene study: J. Mol Med (2008) 86: pp. 1153-1161.
Takehiko Takayanagi et al.: Role of Epidermal Growth Factor Receptor and Endoplasmic Reticulum Stress in Vascular Remodeling Induced by Angiotensin II: Author manuscript: Hypertension. Jun. 2015 ; 65(6): 1349-1355. doi:10.1161/HYPERTENSIONAHA. 115.05344.
William J. Welch, et al.: Role of Extracellular Superoxide Dismutase in the Mouse Angiotensin Slow Pressor Response: Nov. 2006. pp. 934-941.
Elisa Nuti, et al.: Selective Arylsulfonamide Inhibitors of ADAM-17: Hit Optimization and Activity in Ovarian Cancer Cell Models: Journal of Medicinal Chemistry: 2013, 56; pp. 8089-8103.
Masaki Imanishi, et al.: Smooth muscle cell-specific Hif-1 a deficiency suppresses angiotensin II-induced vascular remodelling in mice: Cardiovascular Research (2014) 102, pp. 460-468.
Ira Tabas: The Role of Endoplasmic Reticulum Stress in the Progression of Athero-sclerosis: NIH Public Access Author Manuscript pp. 1-21: Published in final edited form as: Circ Res. Oct. 1, 2010; 107(7): 839-850. doi:10.1161/CIRCRESAHA.110.224766.
Matthias Canault, el al.: The TNF alpha converting enzyme (TACE/ADAM17) is expressed in the atherosclerotic lesions of apolipoprotein E-deficient mice: Possible contribution to elevated plasma levels of soluble TNF alpha receptors: Atherosclerosis 187: 2006. pp. 82-91.
Marie Briet, el al.: Treatment of Arterial Remodeling in Essential Hypertension: Curr Hypertens Rep (2013): 15: pp. 3-9.

* cited by examiner

SEQUENCE LISTING

<160> NUMBER OF SEQ ID NOS: 6

<210> SEQ ID NO 1
<211> LENGTH: 454
<212> TYPE: PRT

<213> ORGANISM: Artificial Sequence
<220> FEATURE:
<223> OTHER INFORMATION: Synthetic: A9(B8) Heavy chain

<400> SEQUENCE: 1

```
Gln Val Thr Leu Lys Glu Ser Gly Gly Leu Phe Gln Pro Gly Gly
1               5                   10                  15

Ser Leu Arg Leu Ser Cys Ala Ala Ser Gly Phe Thr Phe Ser Asn Tyr
            20                  25                  30

Trp Met Tyr Trp Val Arg Gln Ala Pro Gly Lys Gly Pro Glu Trp Val
        35                  40                  45

Ala Thr Ile Lys Gln Asp Gly Ser Asp Lys Tyr Tyr Val Asp Ser Val
    50                  55                  60

Lys Gly Arg Phe Thr Ile Ser Arg Asp Asn Thr Lys Asn Ser Leu Tyr
65                  70                  75                  80

Leu Gln Met Asn Ser Leu Arg Ala Asp Asp Thr Ala Met Tyr Tyr Cys
                85                  90                  95

Ala Arg Ser Arg Glu Arg Tyr Ser Val Asp Ser Tyr Leu Pro Leu His
            100                 105                 110

Tyr Tyr Met Asp Val Trp Gly Arg Gly Thr Met Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Asn Phe Gly Thr Gln Thr
        195                 200                 205

Tyr Thr Cys Asn Val Asp His Lys Pro Ser Asn Thr Lys Val Asp Lys
    210                 215                 220

Thr Val Glu Arg Lys Cys Cys Val Glu Cys Pro Pro Cys Pro Ala Pro
225                 230                 235                 240

Pro Val Ala Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
    290                 295                 300

Ser Thr Phe Arg Val Val Ser Val Leu Thr Val Val His Gln Asp Trp
305                 310                 315                 320

Leu Asn Gly Lys Glu Tyr Lys Cys Lys Val Ser Asn Lys Gly Leu Pro
                325                 330                 335

Ala Pro Ile Glu Lys Thr Ile Ser Lys Thr Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
```

```
                385                 390                 395                 400
Thr Pro Pro Met Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro Gly Lys
                450

<210> SEQ ID NO 2
<211> LENGTH: 216
<212> TYPE: PRT
<213> ORGANISM: Artificial Sequence
<220> FEATURE:
<223> OTHER INFORMATION: Synthetic: A9(B8) Light chain

<400> SEQUENCE: 2

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Arg Leu Pro Gly Ala Ala Pro Gln Leu Leu
            35                  40                  45

Ile Tyr Asn Asn Asp Gln Arg Pro Ser Gly Ile Pro Asp Arg Phe Ser
        50                  55                  60

Gly Ser Lys Ser Gly Thr Ser Gly Ser Leu Val Ile Ser Gly Leu Gln
65                  70                  75                  80

Ser Glu Asp Glu Ala Asp Tyr Tyr Cys Ala Ser Trp Asp Asp Ser Leu
                85                  90                  95

Asn Gly Arg Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
        210                 215

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
ggcgcgggag ggagaagttt                                              20
```

```
<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
cgccgcctca tgttcccgtc                                                    20

<210> SEQ ID NO 5
<211> LENGTH: 21
<212> TYPE: DNA
<213> ORGANISM: Artificial Sequence
<220> FEATURE:
<223> OTHER INFORMATION: Synthetic primer

<400> SEQUENCE: 5
agttccagca cattttgcga g                                                  21

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6
tcatcctccg tgagttctcc a                                                  21
```

METHOD OF MITIGATING CARDIOVASCULAR HYPERTROPHY AND PERIVASCULAR FIBROSIS INDUCED BY ANGIOTENSIN II

CROSS REFERENCE TO A RELATED APPLICATION

This application claims priority from provisional application 62/530903 filed on Jul. 11, 2017, the contents of which are incorporated herein by reference.

SEQUENCE LISTINGS

This application includes sequence listing SEQ ID NO:1 and SEQ ID NO:2.

FIELD OF THE INVENTION

The present invention relates to methods of obviating of hypertensive complications such as cardiovascular hypertrophy and fibrosis by suppressing ADAM 17 expression.

BACKGROUND

The prevalence and morbidity of hypertension is growing steadily[1]. End-organ damage is the most important clinical consequence of hypertension causing cardiac failure, renal failure and stroke. Despite great achievements in blood pressure therapy, optimally treated hypertensive patients still have a 50% greater risk than untreated normotensive subjects[2] suggesting the urgent need of add-on therapy to specifically target hypertensive end-organ damage. Vascular remodeling has been strongly implicated in hypertensive end-organ damage and associated with poor cardiovascular outcomes.

The remodeling predisposes to end-organ damage and pharmacological intervention in vascular remodeling should have special clinical efficacy for prevention of hypertensive organ damage[3]. The renin angiotensin system has been strongly implicated in hypertension and its complications. Importantly, it has been suggested that the mechanisms by which angiotensin II (AngII) elevates blood pressure and enhances cardiovascular remodeling and end-organ damage may be distinct[4] Although many downstream signaling cascades and target genes/proteins of AngII have been identified, the proximal key event primarily responsible for vascular remodeling such as vascular hypertrophy and fibrosis, independent of blood pressure, remains largely unclear[5,6]

AngII mediates vascular smooth muscle cell (VSMC) contraction via $G_q$-mediated intracellular $Ca^{2+}$ elevation and $Gi_2/i_3$-mediated Rho kinase activation[7]. ADAM (a disintegrin and metalloproteinase) proteins belong to a family of membrane spanning metalloprotainases that cleave ectodomains of several substrates including epidermal growth factor receptor (EGFR) ligands[8]. We have shown that ADAM17-mediated EGFR transactivation via heparin-binding EGF-like growth factor (HB-EGF) shedding is required for extracellular signal-regulated kinase (ERK) activation but not for intracellular $Ca^{2+}$ elevation or Rho kinase activation[9-11]. Also, ADAM17 expression is enhanced in neointima after angioplasty, and dominant-negative ADAM17 gene-transfer prevents neointimal hyperplasia[12,] Others have shown that ADAM17 expression is enhanced in atherosclerosis[13] and in the left ventricle upon AngII infusion[14] and that an ADAM17 polymorphism is associated with cardiovascular mortality[15], Odenbach et al in Hypertesion January 2011 pages 123-130 note that RNA interference targeting ADAM 17 (also known as TACE) attenuated angiotensin II up regulation of MMP-2 and prevented development of hypertension as well as development of cardiac hypertrophy and fibrosis but suggested that whereas hypertension might be dependent on both MMP-2 and either ADAM 17 or MMP 7, hypertrophy and fibrosis might involve only ADAM 17 or MMP-7 and not involve MMP-2. US Patent Publication 2008/0317763 indicates that antibodies may inhibit activity of ADAMs. However, it has not been suggested previously that vascular ADAM17 manipulation by use of antibodies may have therapeutic potential against hypertensive complications such as cardiac hypertrophy of fibrosis. Therefore, utilizing mice lacking VSMC ADAM17 or treated with a human cross-reactive ADAM17 antibody as well as with in vitro fibrosis assessment, we have tested our hypothesis that vascular ADAM17 is indispensable for cardiovascular remodeling but not for hypertension induced by AngII, thus highlighting a unique therapeutic target in hypertension that can be used to supplement conventional treatments of hypertension to minimize cardiovascular hypertrophy.

SUMMARY OF THE INVENTION

Our research provides a means for mediating cardiovascular hypertrophy induced by angiotensin II which comprises suppressing ADAM 17 expression for example by administering a therapeutic dose of an ADAM 17 antibody, such as human-mouse cross-reactive ADAN 17 antibodies, for example A9B8. Similar methods may be used to treat perivascular fibrosis induced by angiotensin II.

Antibody A9B8 is believed to be novel.

BRIEF DESCRIPTION OF THE DRAWINGS

The file of this patent contains at least one drawing or photograph executed in color. Copies of this patent with color drawing(s) or photograph(s) will he provided by the Patent and Trademark Office upon request and payment of necessity fee.

Figure 1A:
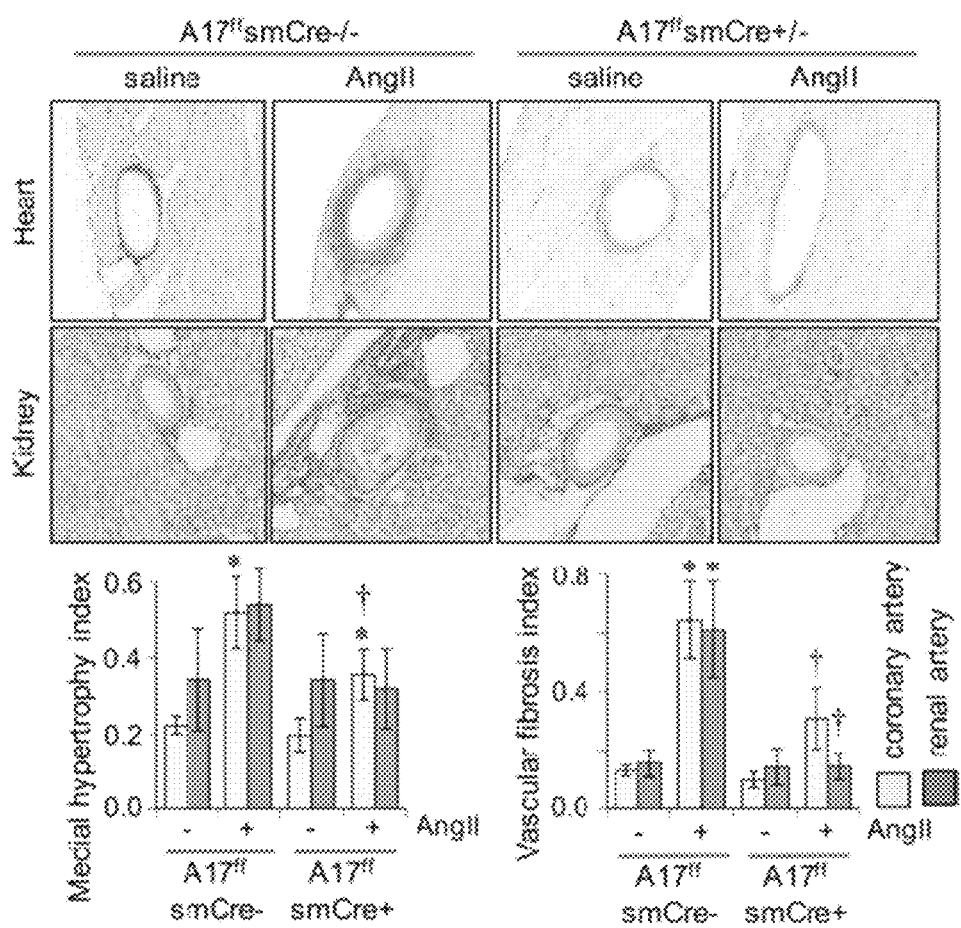
FIG. 1. shows prevention of cardiovascular remodeling in VSMC ADAM17 deficient mice. VSMC ADAM17 deficient mice (A17$^{f/f}$smCre+/−) and control littermate mice (A17$^{f/f}$ ,smCre−/−) were infused with AngII or saline.

The heavy chain of antibody A9B8 has sequence listing SEQ ID NO:1

The light chain of antibody A9B8 has sequence listing SEQ ID NO: 2.

DETAILED DESCRIPTION OF THE INVENTION

The present invention provides a method for reducing or preventing vascular hypertrophy and perivascular fibrosis but not hypertension in patients in need thereof which can be used independently of or in conjunction with treatments of hypertension by administration of an ADAM17 inhibitory antibody to a subject in need thereof. AngII infusion showed vascular ADAM17 induction, EGFR activation and ER stress, which were attenuated in mice trated with such antibodies. Cultured vascular smooth muscle cells were utilized to confirm the involvement of the ADAM17/EGFR signaling axis in induction of vascular fibrosis.

Analysis of blood pressure and vascular pathology in the heart, kidney and aorta with ADAM17 inhibition by an antibody established a role for this metalloproteinase in AngII-induced pathological vascular remodeling independent of hypertension in mice thereby indicating the suitability of the method of the present invention for treatment of vascular pathology in the heart kidneys and aorta.

Antibodies suitable for use in the present invention are human and mouse cross-reactive ADAM 17nhibitory antibodies and include A9B8. Antibody A9B8 is available from Prof. Hang Fai Kwok's research group at the faculty of Health Sciences (FHS) University of Macau.

Such antibodies may be administered to subjects in need thereof by conventional methods for administration of antibodies such as subcutaneous or intravenous injection. Such antibodies are typically administered at dosages of from 1-50 mg/kg every three days, more commonly in the range 3-20 mg/kg every three days, for example in the range 8-12 mg/kg every three days. The antibody is typically administered in a saline or dextrose solution (for example a 5% dextrose solution) at a concentration of from 100-500 nmol/liter, preferably 150-350 nmol/liter, for example about 250 nmol/liter.

Treatment will typically last for from 1 to 30 days but will depend upon the condition of the patient. For example in some cases a treatment of from 3 to 15 days, such as from 5 to 10 days may be sufficient.

As noted above, the method of the present invention may be used in combination with a treatment for hypertension. Such treatments may include life-style changes to take more exercise and reduce stress and also medications such as diuretics, including thiazides, chlorthalidone, and indapamide; beta-blockers and alpha-blockers; calcium-channel blockers; central agonists; peripheral adrenergic inhibitors; vasodilators; angiotensin-converting enzyme (ACE) inhibitors; and angiotensin receptor blockers.

EXPERIMENTS

Animal Studies and the Tissue Analysis

Animal procedures were performed in accordance with National Institutes of Health (NIH) Guide for the Care and Use of Laboratory Animals and Temple University IACUC guidelines. 8-10 week old male ADAM17$^{flox/flox}$ sm22aCre+/− mice[16] and control ADAM17$^{flox/flox}$ sm22aCre−/− mice were infused with AngII (Bachem, 1 μg/kg/min) for 2 weeks via osmotic mini-pump[17]. 8-10 week old male C57Bl6 mice (Jackson) were infused with AngII (Bachem, 1 μg/kg/min) and treated with human cross-reactive ADAM17 inhibitory antibody A9B8[18] or control human IgG2 (Athens Research & Technology) which was solubilized in PBS, 10 mg/kg/day intraperitoneal injection, at day 1 and day 7. Blood pressure and heart rate were evaluated in the conscious state by telemetry (DSI equipped with ADInstrument 6 software) via carotid catheter (PA-C10 transmitter). Cardiac function was measured using VisualSonics Velvo 2100 (M-mode). Plasma B type natriuretic peptide and blood urea nitrogen concentrations were determined by the EIA kits (RayBiotech Inc. and Stanbio Laboratories, respectively). Extracted hearts, kidneys and aortas were fixed and used for histological studies as described previously[19]

To evaluate vascular hypertrophy and perivascular fibrosis in hearts and kidneys, serial cross-sections (5 μm thick) were stained in Sirius Red (EMS, Hatfield PA). Briefly, after de-paraffinization and re-hydration, sections were stained in equal parts Weigert's Iron Hematoxylin A and B (EMS, Hatfield PA) for 10 min at room temperature. Sections were then washed twice in distilled water for 3 min per wash. Sirius Red was added for 1 h at room temperature. Slides were washed twice in 0.01 N HCl for 3 min per wash. Sections were then dehydrated and penetrated using ethanol and xylene, respectively. Thoracic aortas were stained with Masson's trichrome protocol to distinguish medial area from adventitia. Briefly, after de-paraffinization and re-hydration, sections were incubated with Bouin's fluid for 1 h at 56° C., Sections were washed three times in distilled water for 3 min per wash and then incubated with Working HE solution for 7.5 min followed by washing in distilled water for 30 sec, Sections were then incubated with Biebrich Scarlet-Acid Fuchsin solution for 1 h at 56° C. After incubation with phosphotungstic-phosphomolybdic acid solution for 5 min, sections were stained with Aniline Blue stain solution for 5 min. Sections were washed in 1% acetic acid for 30 sec and distilled water for 30 sec. Sections were then dehydrated and penetrated using ethanol and xylene, respectively. Images were visualized on an Olympus IX81 inverted microscope using an Olympus SC30 high resolution camera and were acquired with Olympus cellSens Entry 1.11 software. Analysis was conducted using ImageJ 1.50 f software (rsb.info.nih.gov/ij).

To calculate vascular hypertrophy in the heart and kidney, the value of medial area was divided by the true area of the vessel. True area was calculated by vessel outer perimeter$^2$ divided by 4n. The value generated was the area of the vessel in true circular form. To calculate perivascular fibrosis, the value of fibrosis area was subtracted from vessel area and divided by the true area of the vessel. In total, 6-8 randomly selected samples per group were used for analysis. 3 representative vascular images were analyzed per sample, Medial hypertrophy of thoracic aorta was quantified by measurements of medial thickness in 4 randomly-selected locations per slide. 3 representative vascular images were analyzed per sample. Adventitia of the aorta was not quantified as the area was occasionally damaged or removed during the dissection.

For immunohistochemistry (IHC), serial cross-sections were deparaffinized and blocked in 5% goat serum and 1% BSA for 1 h at room temperature, incubated with primary antibody in PBS containing 1% BSA and 0.1% Tween 20 for 18 h at 4° C., followed by biotinylated secondary antibody for 90 min at room temperature. Slides were incubated with avidin-biotin peroxidase complex for 30 min at room temperature and staining was visualized with the substrate diaminobenzidine (Vector) producing a brown color and counterstained with haematoxylin. An equal concentration of control IgG was used side-by-side with each antibody to ensure staining specificity[19]. Quantification of the antibody staining was performed as reported previously with subtraction of the IgG background staining[19] All images were visualized on Olympus SC30 high resolution camera and were acquired with Olympus cellSens Entry 1.11 software using the same exposure time. Images were loaded into the ImageJ program for analysis. A vascular region of interest was drawn around the coronary arteries with the freehand selection tool. Adventitia was excluded from the quantification, since the adventitial areas were quite limited in the arteries, except those with AngII infusion alone. All images were set to the same hue, saturation and brightness. The area and intensity (optical density) in the region of interest were then measured and analyzed. Data were obtained from 4 mice in each group with 3 to 4 non-overlapping high power fields for each antibody.

To evaluate ADAM17 mRNA expression, thoracic aortas and hearts were homogenized using BioMasher (Takara) and total RNA was extracted using TR Izol reagent (Invitrogen), cDNA was synthesized with RevertAid First Strand cDNA Synthesis Kit (Thermo). Quantitative real-time PCR (qPCR) was performed with SYBR Green qPCR Master Mix (Fermentas) as described previously[20]. mRNA abundance was calculated by normalization to ribosome 18S. The primers used were ADAM17: Forward GGC GCG GGA GGG AGA AGT TT, Reverse CGC CGC CTC ATG TTG CCG TC, Ribosome 18S: Forward AGT TCC AGC ACA TTT TGC GAG, Reverse TCA TCC TCC GTG AGT TCT CCA.

Cell Culture and Experiments

VSMCs were prepared from thoracic aortas of male Sprague-Dawley rats by the explant method as described previously[21]. VSMCs were subcultured in DMEM containing 10% fetal bovine serum, penicillin and streptomycin. Cells from passage 3 to 10 at 80~90% confluence were made quiescent by incubation with serum-free medium for 2-3 days.

To avoid any potential phenotypic alteration, VSMCs were renewed every 2-3 months and VSMCs from frozen stock were never used. The results were confirmed in at least 2 distinct cell preparations.

Immunoblotting (IB) was performed as previously described[21]. Quiescent VSMCs grown on 6-well plates were stimulated with 100 nM AngII (Sigma) for specified durations. The reaction was terminated by the replacement of medium with 100 μL of 1×SDS lysis buffer. 40 μL of the cell lysates were subjected to SDS-PAGE gel electrophoresis and electrophoretically transferred to a nitrocellulose membrane. The membranes were then exposed to primary antibodies overnight at 4° C. After incubation with the peroxidase linked secondary antibody for 1 h at room temperature, immunoreactive proteins were visualized using a chemiluminescence reaction kit.

To evaluate pro-fibrotic response, serum-starved VSMCs were stimulated with 100 nM AngII for 48 hours and extracellular cellular collagen content was quantified by Sirius Red collagen quantification kit (Chondrex) according to the manufacture's protocol. Recombinant adenoviral vector encoding rat ADAM17 siRNA was created and specificity and efficiency has been reported[11]. VSMCs were infected with 100 m.o.i. adenovirus prior to the AngII stimulation as reported previously[11]. ADAM17 selective inhibitor compound #21 (JG26)[8] was generated as reported. VSMCs were pretreated with 1 μmol/L JG26 or vehicle (0.1% DMSO in final) for 30 min prior to the AngII stimulation. 4-phenylbutyrate (PBA) was obtained from Scandinavian Formulas and solubilized in DMEM. VSMCs were pretreated with 10 mmol/L PBA for 30 min.

Erlotinib (OSI Pharmaceuticals) was obtained from Genentech. VSMCs were pretreated with 1 μmol/L erlotinib for 30 min.

Antibodies

Antibodies against $Tyr^{1068}$-phosphorylated EGFR for IHC (2234) and $Ser^{51}$-phosphorylated eIF2a were purchased from Cell Signaling. Antibody against $Tyr^{1068}$- phosphorylated EGFR for IB (44788G) was purchased from Invitrogen. Antibody against KDEL for detection of an ER stress marker GRP78 (ADI-SPA-827) was purchased from Enzo Life Sciences. Antibodies against ADAM17 for IB (sc-13973), EGFR (sc-03) and an ER stress marker, CHOP-10/GADD-153 (sc-575) were purchased from Santa Cruz Biotechnology. Antibodies against ADAM17 for IHC (ab39163) were purchased from Abcam. Antibodies against Cre recombinase (MAB3120) and GAPDH (MAB374) were purchased from Millipore.

Statistical Analysis

Data are presented as mean ±SEM or SD where appropriate. Differences between the multiple groups were analyzed by 1-way or 2-way ANOVA, followed by the Tukey's post hoc test, Statistical significance was set at p<0.05.

RESULTS

Prevention of AngII-induced Cardiovascular Remodeling in Mice Lacking VSMC

ADAM17

VSMC ADAM17 deficient $ADAM17^{flox/flox}$ sm22aCre+/− mice were generated[16] and vascular selective Cre expression was confirmed.

Figure 1B:
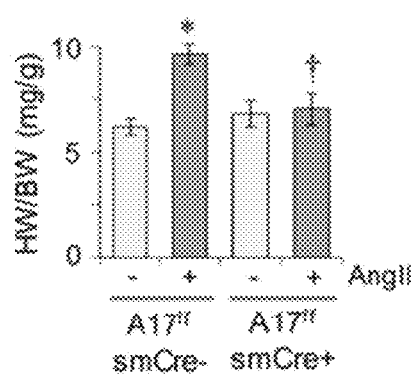
Figure 1C:
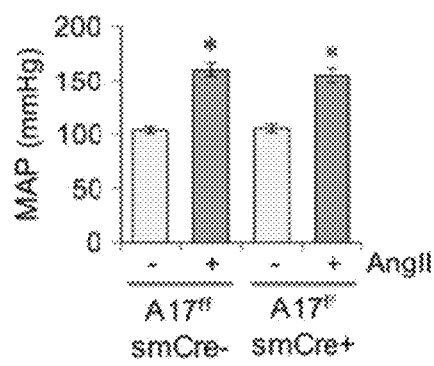
Figure 2:
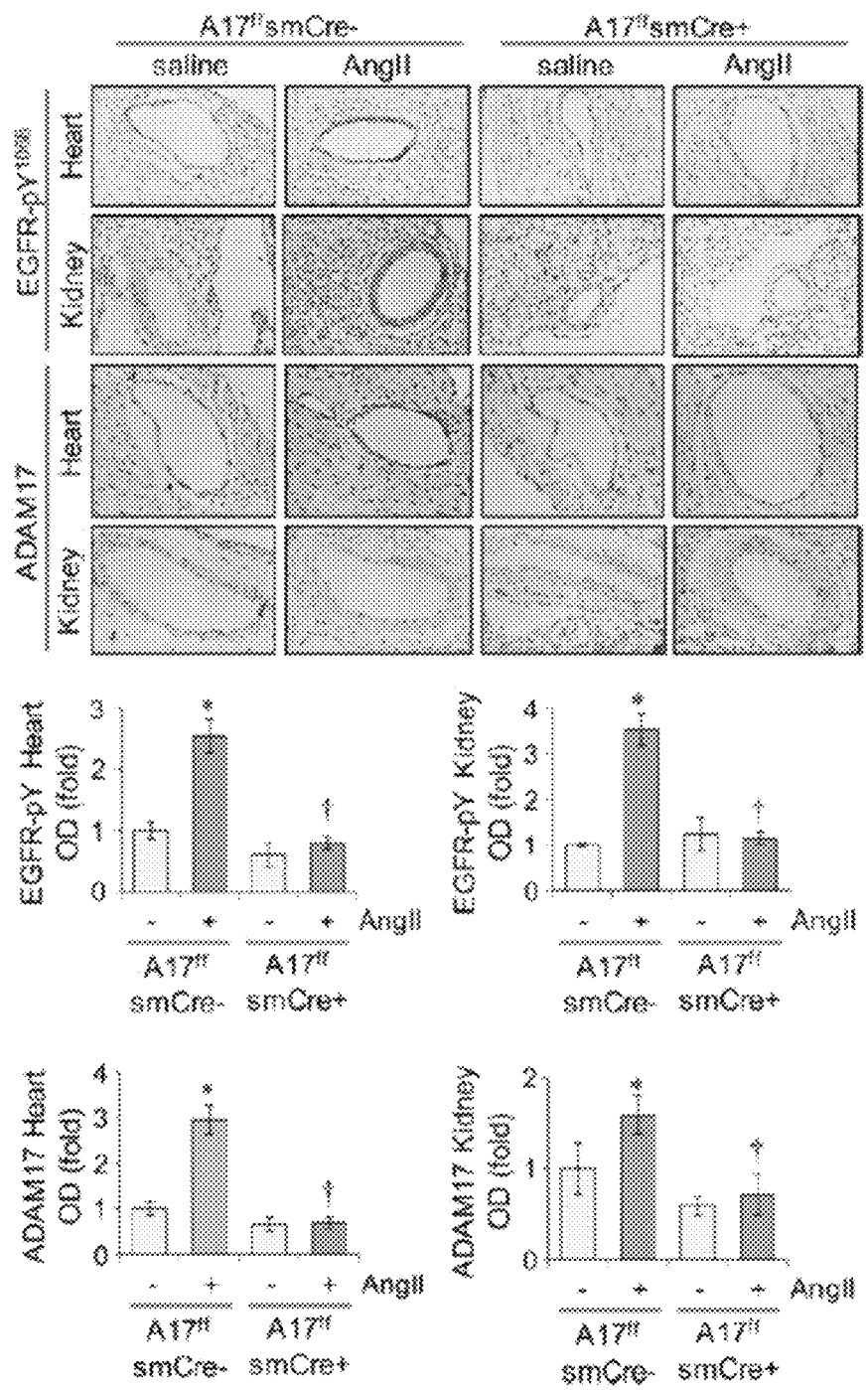
FIG. 2. shows suppression of vascular EGFR activation in VSMC ADAM17 deficient mice. VSMC ADAM17 deficient mice and control mice were infused with AngII or saline as in FIG. 1.

VSMC ADAM17 deficient mice and littermate control $ADAM17^{flox/flox}$sm22aCre−/− mice were infused with 1 μg/kg/min AngII for 2 weeks. In control littermate mice, 2 weeks of AngII infusion caused vascular hypertrophy in aorta and coronary arteries that was markedly prevented in VSMC ADAM17 deficient mice. Perivascular fibrosis induced by AngII infusion was also prevented in VSMC ADAM17 deficient mice (FIG. 1A). In control mice, AngII infusion for 2 weeks induced cardiac hypertrophy assessed by heart weight to body weight ratio and echocardiogram (FIG. 1B). Serum B type natriuretic peptide and blood urea nitrogen concentrations were also elevated in these mice). These cardiac and renal alterations by AngII infusion were attenuated in VSMC ADAM17 deficient mice. In contrast, hypertension was induced in both groups infused with AngII at 2 weeks (FIG. 1C). AngII- induced vascular remodeling in control mice was associated with vascular-dominant EGFR activation and ER stress assessed by immunohistochemistry. These AngII responses were attenuated in VSMC ADAM17 deficient mice. ADAM17 expression was barely detectable in heart or kidney but was significantly induced upon AngII infusion in the vasculature. No such induction was observed in VSMC ADAM17 deficient mice (FIG. 2). qPCR analysis of aortic mRNA confirmed ADAM17 induction by AngII as well as vascular ADAM17 silencing. ADAM17 mRNA was also increased in whole heart with AngII infusion in control mice but not in VSMC ADAM17 deficient mice. In addition, while statistically insignificant, cardiac ADAM17 mRNA expression tends to be less in saline-infused VSMC ADAM17 deficient mice compared with saline-infused control mice.

Figure 3A:
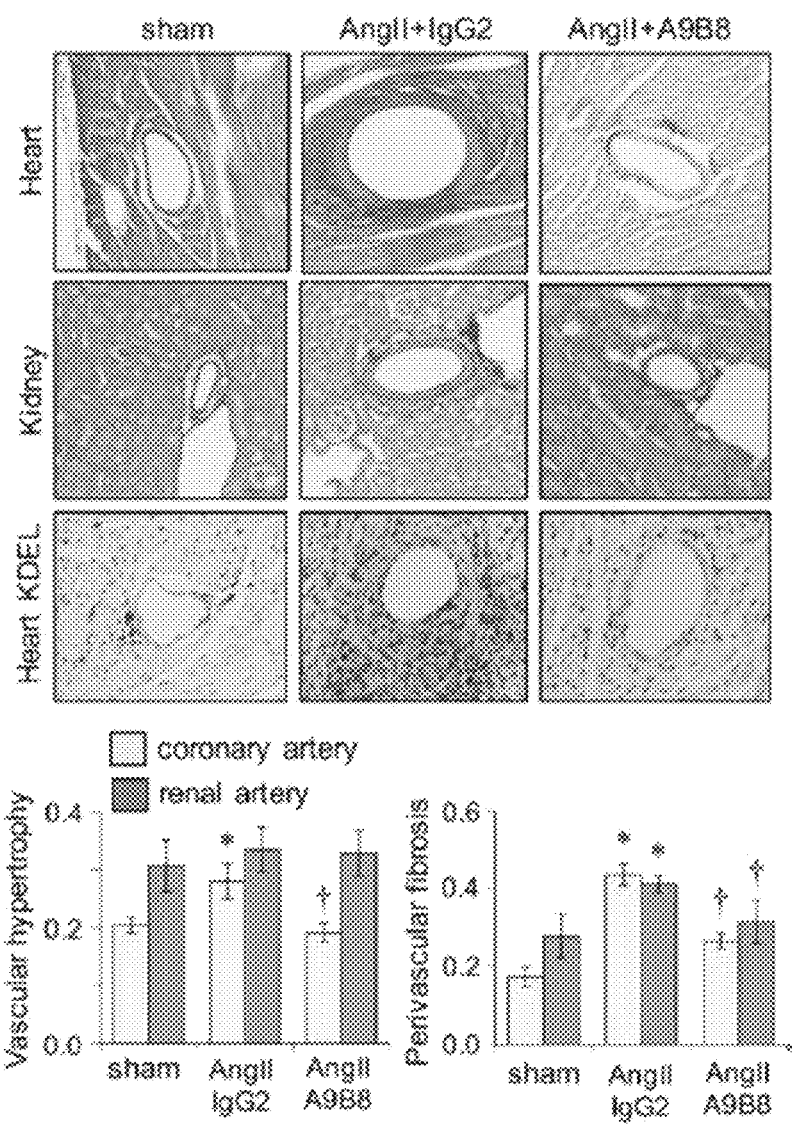
FIG. 3, shows effects of human cross-reactive ADAM17 inhibitory antibody, A9B8, on cardiovascular remodeling induced by AngII.
Figure 3B:
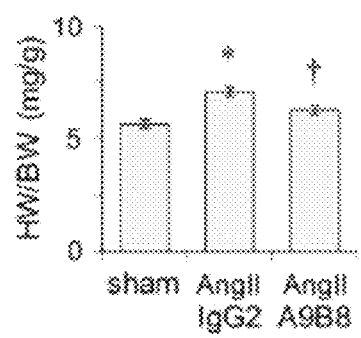
Figure 3C:
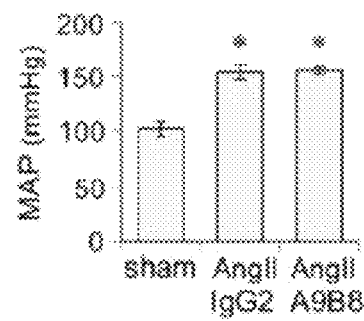

A Human Cross-Reactive ADAM17 Antibody Attenuates Cardiovascular Remodeling Induced by AngII To ascertain that ADAM17 represents a novel therapeutic target contributing to target organ remodeling, AngII-infused C57Bl6 mice were treated with a human cross-reactive ADAM17 inhibitory antibody A9B8[18]. C57BI/6 mice were infused with 1 µg/kg/min AngII for 2 weeks with treatment of ADAM17 antibody or control IgG (10 mg/kg i.p. on day 1 and 7). A9B8 prevented AngII-induced cardiovascular hypertrophy and perivascular fibrosis but not hypertension or its development. These responses were associated with suppression of ER stress (FIG. 3).

Figure 4A:
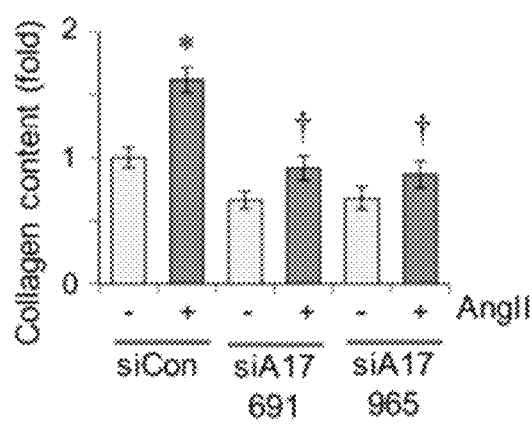
FIG. 4. shows effects of ADAM17 inhibition on pro-fibrosis response in VSMCs induced by AngII.
Figure 4B:
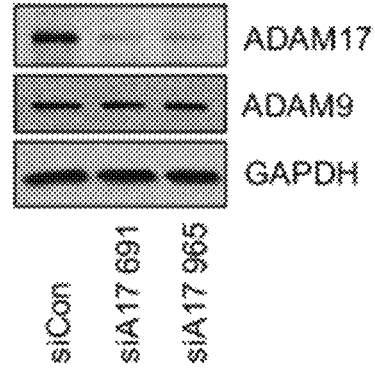
Figure 4C:
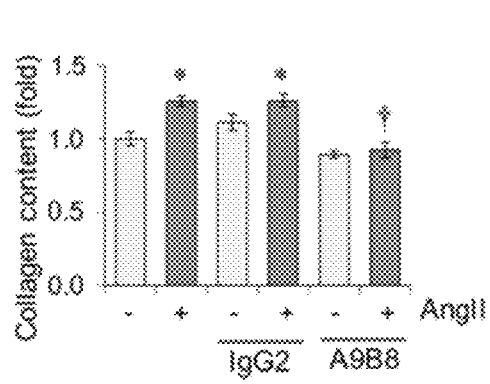
Figure 4D:
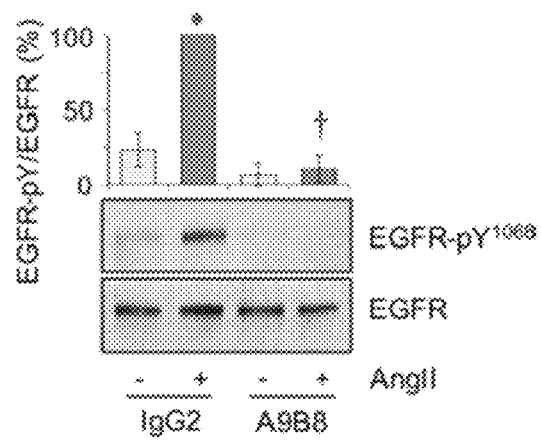

ADAM17 Antibody, a Small Molecule ADAM17 Inhibitor or Adenovirus Encoding ADAM17 Sirna Attenuates a Fibrotic Response Induced by AngII In Vitro To test for the role of ADAM17 in AngII-induced vascular fibrosis, extracellular collagen content was evaluated in VSMCs stimulated with AngII. Adenovirus encoding ADAM17 siRNA[11] attenuated the AngII-induced enhancement in collagen content (FIG. 4A and 4B). Treatment of VSMCs with ADAM17 antibody A9B8, a highly-selective ADAM17 inhibitor JG26/compound 21[22], an EGFR kinase inhibitor erlotinib or a chemical ER chaperone PBA also attenuated AngII-induced enhancement in collagen content (FIG. 4C). As shown with the ADAM17 siRNA[11], A9B8 as well as JG26 inhibited AngII-induced EGFR transactivation assessed with an auto-phosphorylation site antibody (FIG. 4D).

Discussion

It is intriguing that VSMC silencing of ADAM17 or pharmacological inhibition of ADAM17 further prevented vascular fibrosis induced by AngII in vivo and in vitro. Faint expression of ADAM17 under normal conditions and enhanced expression in areas of interstitial fibrosis in damaged kidneys in humans has been reported[23] Additionally, cardiac specific HB-EGF transgenic mice develop cardiac fibrosis[24] AngII-induced renal interstitial fibrosis is attenuated in proximal tubule EGFR deficient mice[25] In our 2 week AngII infusion model, interstitial fibrosis in the heart or kidney was too marginal to be evaluated. However, it is likely that the paracrine production of HB-EGF and activation of EGFR via induction and activation of ADAM17 in VSMCs may be critical for development of perivascular fibrosis associated with hypertension[17,26].

In a study on which the present invention is based with AngII infused mice treated with an ADAM17 inhibitory antibody, hypertension was induced within a few days with blood pressure values comparable to the control mice. The values are also in agreement with reported values in C57Bl6 background mice with AngiI infusion [27] While these data suggest that ADAM17 inhibition or silencing has no alteration of the development of hypertension in response to AngII, lack of continued blood pressure recording is a limitation of the present study. This study could also include an additionally important ADAM17Wild/Wild sm22Cre+/− control mouse group since endogenous lox-like sites are known to cause Cre- dependent chromosomal rearrangement in a Cre-transgenic mouse in the absence of loxP sequences[28]. Although the protocol is different, control sm22aCre+/− mice develop hypertension, cardiac hypertrophy and vascular fibrosis in response to AngII infusion[29].

The applicant has confirmed vascular dominant expression of the Cre transgene and intact presser responses to AngII in VSMC ADAM17 deficient mice or ADAM17 antibody-treated mice. However, contribution of VSMC ADAM17 to AngII-induced cardiac hypertrophy may require additional confirmation. Although lesser than smooth muscle, the sm22a promoter driver could show transgene expression in cardiac myocytes[30] There is a tendency of cardiac ADAM17 reduction in ADAM17$^{flox/flox}$sm22aCre+/− mice, which could be due to a combination of VSMC and cardiac myocyte silencing in the heart according to literature[31]. While the present study suggests that vascular-dominant ADAM17 and EGFR activation may mediate cardiac hypertrophy induced by AngII, cardiac myocyte-targeted expression of dominant-negative EGFR inhibits cardiac hypertrophy induced by AngII[32] Therefore, future experiments in cardiac myocyte specific ADAM17 deficient mice should be conducted to test the role of cardiac myocyte ADAM17 in cardiac hypertrophy induced by AngII.

ER stress has been implicated in cardiovascular diseases[33], whereas limited information is available for its role in hypertension[34] Our recent study suggests a potential prevention of hypertensive organ damage but not hypertension by PBA, which seems to involve VSMC ADAM17 as well as EGFR[17]. Inhibition of the fibrotic response in VSMCs with ER stress inhibition further suggests the presence of ER stress-responsible downstream signal transduction leading to vascular fibrosis, which likely involves transcriptional up-regulation of several distinct genes[17,20].

References

1. Egan B M, Li J, Hutchison F N, Ferdinand K C. Hypertension in the United States, 1999 to 2012: progress toward healthy people 2020 goals. Circulation. 2014;130: 1692-1699.
2. Struthers A D, George J. High B-Type Natriuretic Peptide Hypertensives at Target Blood Pressure: Potential Role of beta-Blockers to Reduce Their Elevated Risk. Hypertension. 2015;66:927-932.
3. Briet M, Schiffrin E L. Treatment of arterial remodeling in essential hypertension. Curr Hypertens Rep. 2013;15:3-9.
4. Weir M R. Effects of renin-angiotensin system inhibition on end-organ protection: can we do better? Clin Ther, 2007;29:1803-1824.
5. Montezano A C, Nguyen Dinh Cat A, Rios F J, Touyz R M. Angiotensin H and vascular injury. Curr Hypertens Rep. 2014;16:431.
6. Te Riet L, van Esch J H, Roks A J, van den Meiracker A H, Danser A H. Hypertension: renin-angiotensin-aldosterone system alterations. Circ Res. 2015;116:960-975.
7. Kanaide H, Ichiki T, Nishimura J, Hirano K. Cellular mechanism of vasoconstriction induced by angiotensin II: it remains to be determined. Circ Res. 2003;93:1015- 1017,
8. Blobel C P. ADAMs: key components in EGFR signalling and development. Nat Rev Mol Cell Biol, 2005;6:32-43,
9. Ohtsu H, Dempsey P J, Frank G D, Brailoiu E, Higuchi S, Suzuki H, Nakashima H, Eguchi K, Eguchi S. ADAM17 mediates epidermal growth factor receptor transactivation and vascular smooth muscle cell hypertrophy induced by angiotensin II. Arterioscler Thromb Vasc Biol. 2006;26: e133-137.
10. Ohtsu H, Higuchi S, Shirai H, Eguchi K, Suzuki H, Hinoki A, Brailoiu E, Eckhart A D, Frank G D, Eguchi S. Central role of Gq in the hypertrophic signal transduction of angiotensin II in vascular smooth muscle cells, Endocrinology. 2008;149:3569- 3575.
11. Elliott K J, Bourne A M, Takayanagi T, Takaguri A, Kobayashi T, Eguchi K, Eguchi S. ADAM17 silencing by adenovirus encoding miRNA-embedded siRNA revealed essential signal transduction by angiotensin II in vascular smooth muscle cells. J Mol Cell Cardiol. 2013;62:1-7.

12. Takaguri A, Kimura K, Hinoki A, Bourne A M, Autieri M V, Eguchi S. A disintegrin and metalloprotease 17 mediates neointimal hyperplasia in vasculature. Hypertension. 2011;57:841-845.

13. Canault M, Peiretti F, Kopp F, Bonardo B, Bonzi M F, Coudeyre J C, Alessi M C, Juhan-Vague I, Nalbone G. The TNF alpha converting enzyme (TACE/ADAM17) is expressed in the atherosclerotic lesions of apolipoprotein E-deficient mice: possible contribution to elevated plasma levels of soluble TNF alpha receptors. Atherosclerosis. 2006;187:82-91.

14. Patel V B, Clarke N, Wang Z, Fan D, Parajuli N, Basu R, Putko B, Kassiri Z, Turner A J , Oudit G Y. Angiotensin II induced proteolytic cleavage of myocardial ACE2 is mediated by TACE/ADAM-17: A positive feedback mechanism in the RAS. J Mol Cell Cardiol. 2014;66:167-176.

15. Morange P E, Tregouet D A, Godefroy T, Saut N, Bickel C, Rupprecht H J, Lackner K, Barbaux S, Poirier 0, Peiretti F, Nalbone G, Juhan-Vague I, Blankenberg 5, Tiret L. Polymorphisms of the tumor necrosis factor-alpha (TNF) and the TNF- alpha converting enzyme (TACE/ADAM17) genes in relation to cardiovascular mortality: the Athero-Gene study. J Mol Med (Berl). 2008;86:1153-1161, 16. Weskamp G, Mendelson K, Swendeman S, Le Gall S, Ma Y, Lyman 5,
Hinoki A, Eguchi 5, Guaiquil V, Horiuchi K, Blobel C P. Pathological neovascularization is reduced by inactivation of ADAM17 in endothelial cells but not in pericytes. Circ Res. 2010;106:932-940.

17. Takayanagi T, Kawai T, Forrester S J, Obama T, Tsuji T, Fukuda Y, Elliott K J, Tilley D G, Davisson R L, Park J Y, Eguchi S, Role of Epidermal Growth Factor Receptor and Endoplasmic Reticulum Stress in Vascular Remodeling Induced by Angiotensin II. Hypertension. 2015;65:1349-1355.

18. Kwok H F, Botkjaer K A, Tape C J, Huang Y, McCafferty J, Murphy G. Development of a 'mouse and human cross-reactive' affinity-matured exosite inhibitory human antibody specific to TACE (ADAM17) for cancer immunotherapy. Protein Eng Des Sel. 2014;27:179-190.

19. Takayanagi T, Crawford K J, Kobayashi T, Obama T, Tsuji T, Elliott K J, Hashimoto T, Rizzo V, Eguchi S. Caveolin-1 is critical for abdominal aortic aneurysm formation induced by angiotensin II and inhibition of lysyl oxidase, Clin Sci, 2014;126:785-794.

20. Obama T, Tsuji T, Kobayashi T, Fukuda Y, Takayanagi T, Taro Y, Kawai T, Forrester S J, Elliott K J, Choi E, Daugherty A, Rizzo V, Eguchi S. Epidermal growth factor receptor inhibitor protects against abdominal aortic aneurysm in a mouse model. C/in Sci (Land). 2015;128:559-565.

21. Takaguri A, Shirai H, Kimura K, Hinoki A, Eguchi K, Carlile-Klusacek M, Yang B, Rizzo V, Eguchi S. Caveolin-1 negatively regulates a metalloprotease-dependent epidermal growth factor receptor transactivation by angiotensin II. J Mol Cell Cardiol, 2011;50:545-551.

22. Nuti E, Casalini F, Santamaria S, Fabbi M, Carbotti G, Ferrini S, Marinelli L,
La Pietra V, Novellino E, Camodeca C, Orlandini E, Nencetti S, Rossello A. Selective arylsulfonamide inhibitors of ADAM-17: hit optimization and activity in ovarian cancer cell models. J Med Chern. 2013;56:8089-8103.

23. Melenhorst W B, Visser L, Timmer A, van den Heuvel M C, Stegeman C A, van Goor H. ADAM17 upregulation in human renal disease: a role in modulating TGF-alpha availability? Am J Physio/ Renal Physiol. 2009;297:F781-790.

24. Lian H, Ma Y, Feng J, Dong W, Yang Q, Lu D, Zhang L. Heparin-binding EGF-like growth factor induces heart interstitial fibrosis via an Akt/mTor/p70s6k pathway, PLoS One. 2012;7;e44946.

25. Chen J, Chen J K, Nagai K, Plieth D, Tan M, Lee T C, Threadgill D W, Neilson E G, Harris R C. EGFR signaling promotes TGFbeta-dependent renal fibrosis. J Am Soc Nephroi. 2012;23:215-224.

26. Forrester S J, Kawai T, O'Brien 5, Thomas W, Harris R C, Eguchi S. Epidermal Growth Factor Receptor Transactivation: Mechanisms, Pathophysiology, and Potential Therapies in the Cardiovascular System. Annu Rev Pharmacal Toxicoi, 2016;56:627-653.

27. Welch W J, Chabrashvili T, Solis G, Chen Y, Gill P S, Aslam S, Wang X, Ji H, Sandberg K, Jose P, Wilcox C S. Role of extracellular superoxide dismutase in the mouse angiotensin slow pressor response. Hypertension. 2006;48:934-941.

28. Schmidt E E, Taylor D S, Prigge J R, Barnett S, Capecchi M R, Illegitimate Cre-dependent chromosome rearrangements in transgenic mouse spermatids. Proc Natl Acad Sci U S A. 2000;97:13702-13707.

29. Imanishi M, Tomita S, Ishizawa K, Kihira Y, Ueno M, Izawa-Ishizawa Y, Ikeda Y, Yamano N, Tsuchiya K, Tamaki T. Smooth muscle cell-specific Hif-1alpha deficiency suppresses angiotensin H-induced vascular remodelling in mice. Cardiovasc Res, 2014;102:460-468.

30. Lepore J J, Cheng L, Min Lu M, Mericko P A, Morrisey E E, Parmacek M S. High-efficiency somatic mutagenesis in smooth muscle cells and cardiac myocytes in SM22alpha-Cre transgenic mice. Genesis. 2005;41:179-184.

31. Schreier B, Rabe S, Schneider B, Bretschneider M, Rupp S, Ruhs S, Neumann J, Rueckschloss U, Sibilia M, Gotthardt M, Grossmann C, Gekle M. Loss of epidermal growth factor receptor in vascular smooth muscle cells and cardiomyocytes causes arterial hypotension and cardiac hypertrophy. Hypertension. 2013;61:333-340.

32, Zhai P, Galeotti J, Liu J, Halle E, Yu X, Wagner T, Sadoshima J. An angiotensin II type 1 receptor mutant lacking epidermal growth factor receptor transactivation does not induce angiotensin II-mediated cardiac hypertrophy. Circ Res. 2006;99:528-536.

33. Tabas I. The role of endoplasmic reticulum stress in the progression of atherosclerosis. Circ Res. 2010;107:839-850.

34. Spitler K M, Webb R C. Endoplasmic Reticulum Stress Contributes to Aortic
Stiffening via Proapoptotic and Fibrotic Signaling Mechanisms, Hypertension, 2013;63:e40-e45.

What I claim is:

1. A method of treating cardiovascular hypertrophy induced by angiotensin II which comprises suppressing ADAM 17 activity by administering a therapeutic dose of antibody A9B8 to a subject in need thereof.

2. The method of claim 1 wherein said treatment treats vascular pathology in the heart, kidney or aorta.

3. The method of claim 1 wherein said treatment is combined with treatment of hypertension.

4. A method of treating perivascular fibrosis induced by angiotensin II which comprises suppressing ADAM 17 activity by administering a therapeutic dose of antibody A9B8 to a subject in need thereof.

5. The method of claim 4 wherein said treatment treats vascular pathology in the heart, kidney or aorta.

6. The method of claim 4 wherein said treatment is combined with treatment of hypertension.

7. The antibody A9B8.

* * * * *